US012779245B2

(12) United States Patent
Herekar et al.

(10) Patent No.: US 12,779,245 B2
(45) Date of Patent: Nov. 3, 2026

(54) SYSTEMS, METHODS, AND APPARATUS FOR OCULAR LASER THERAPY

(71) Applicant: SENOGEN GMBH, Rodgau (DE)

(72) Inventors: Anjali Herekar, Palo Alto, CA (US); Rajeev Herekar, Palo Alto, CA (US); Satish Herekar, Palo Alto, CA (US)

(73) Assignee: SENOGEN GMBH, Rodgau (DE)

( * ) Notice: Subject to any disclaimer, the term of this patent is extended or adjusted under 35 U.S.C. 154(b) by 579 days.

(21) Appl. No.: 18/010,698

(22) PCT Filed: Jun. 23, 2021

(86) PCT No.: PCT/US2021/038597

§ 371 (c)(1),
(2) Date: Dec. 15, 2022

(87) PCT Pub. No.: WO2021/262796

PCT Pub. Date: Dec. 30, 2021

(65) Prior Publication Data

US 2023/0226372 A1 Jul. 20, 2023

Related U.S. Application Data

(60) Provisional application No. 63/126,189, filed on Dec. 16, 2020, provisional application No. 63/043,275, filed on Jun. 24, 2020.

(51) Int. Cl.
*A61N 5/067* (2006.01)
*A61N 5/06* (2006.01)

(52) U.S. Cl.
CPC ...... *A61N 5/067* (2021.08); *A61N 2005/0654* (2013.01); *A61N 2005/0659* (2013.01); *A61N 2005/0667* (2013.01)

(58) Field of Classification Search
CPC ........... A61N 5/067; A61N 2005/0654; A61N 2005/0659; A61N 2005/0667
(Continued)

(56) References Cited

U.S. PATENT DOCUMENTS 5,290,272 A 3/1994 Burstein et al.
5,587,175 A 12/1996 Viegas et al.
(Continued)

FOREIGN PATENT DOCUMENTS

CN 1089127 A 7/1994
CN 104114131 A 10/2014
(Continued)

OTHER PUBLICATIONS

International Search Report issued in PCT Application No. PCT/US2021/038597, mailed Oct. 20, 2021.
(Continued)

*Primary Examiner* — Aaron F Roane
(74) *Attorney, Agent, or Firm* — MARSHALL, GERSTEIN & BORUN LLP

(57) ABSTRACT

Near-infrared/Mid-infrared lasers are used to de-claudicate glaucomatous tissue, translocate extra-ocular muscles, thermally pulsate palpebrae, and permeate/vasodilate superficial/epi-scleral membranes for dmg delivery. Diffractive optic element-mediated laser patterns may irradiate eye tissues under pulsed or continuous wave regimes with programmable durations and sequences for efficient treatments while minimizing adverse effects.

20 Claims, 13 Drawing Sheets

(58) Field of Classification Search
USPC .............................................................. 607/89
See application file for complete search history.

(56) References Cited

U.S. PATENT DOCUMENTS

| | | | |
|---|---|---|---|
| 5,616,139 A | 4/1997 | Okamoto | |
| 2006/0100677 A1 | 5/2006 | Blumenkranz et al. | |
| 2013/0165911 A1 | 6/2013 | Raksi et al. | |
| 2014/0081248 A1 | 3/2014 | Blumenkranz et al. | |
| 2014/0128854 A1 | 5/2014 | McArdle et al. | |
| 2015/0005750 A1 | 1/2015 | Kelleher et al. | |
| 2015/0349150 A1 | 12/2015 | Carey et al. | |
| 2015/0366706 A1 | 12/2015 | Belkin et al. | |
| 2018/0207029 A1* | 7/2018 | Herekar | A61N 5/0625 |
| 2019/0091065 A1 | 3/2019 | Kelleher et al. | |
| 2019/0175407 A1 | 6/2019 | Bacher et al. | |

FOREIGN PATENT DOCUMENTS

| | | |
|---|---|---|
| CN | 105050556 A | 11/2015 |
| JP | 2001514928 A | 9/2001 |
| JP | 2016507321 A | 3/2016 |
| JP | 2017533074 A | 11/2017 |
| JP | 2019514454 A | 6/2019 |
| WO | WO-2006074469 A2 | 7/2006 |
| WO | WO-2017192168 A1 | 11/2017 |
| WO | WO-2019109125 A1 | 6/2019 |

OTHER PUBLICATIONS

Office Action in corresponding Japanese patent application No. 2022-578933, dated Mar. 11, 2025.
Office Action in corresponding Chinese patent application No. 202180044973.3, dated May 14, 2025.
Extended European Search Report for European Patent Application No. 21829648.1 dated May 7, 2024.

* cited by examiner

SYSTEMS, METHODS, AND APPARATUS FOR OCULAR LASER THERAPY

CROSS-REFERENCE

This application claims priority to U.S. Provisional Application No. 63/043,275, filed Jun. 24, 2020 and U.S. Provisional Application No. 63/126,189, filed Mar. 18, 2021, which are incorporated herein by reference.

BACKGROUND

Existing methods and apparatus for treating glaucoma, presbyopia, dry eye disease, diplopia, convergence insufficiency, strabismus, and other ophthalmic conditions can produce less than ideal results.

SUMMARY

It would therefore be desirable to provide more efficient and less costly systems, methods, and apparatus for treating ophthalmic conditions. Not necessarily all such aspects or advantages are achieved by any particular embodiment. Thus, various embodiments may be carried out in a manner that achieves or optimizes one advantage or group of advantages taught herein without necessarily achieving other aspects or advantages as may also be taught or suggested herein.

The present disclosure generally relates to medical devices, and methods and more particularly relates to methods and apparatus for treating the eye.

Aspects of the present disclosure include a system for treating an eye. In some embodiments, the system may comprise: a laser configured to generate a laser beam; and a diffractive optical element configured to split the laser beam into a pre-determined pattern and direct the patterned laser beam to a treatment zone of the eye. In some embodiments, the laser comprises a wavelength range from about 500 nanometers (nm) to about 2 micrometers (μm). In some embodiments, the laser comprises a power from about 100 (milliwatts) mW to about 4 watts (W). In some embodiments, the laser comprises a pulse rep rate from about 1 hertz (Hz) to about 1000 Hz. In some embodiments, the treatment pattern comprises an arcuate, annular, spotted, or line scan pattern. In some embodiments, the spotted treatment pattern comprises at least 2 points of illumination. In some embodiments, the treatment zone of the eye comprises the eyelids, sclera, retina, or any combination thereof. In some embodiments, the system is configured to be handheld or slit lamp adapted. In some embodiments, the patient interface comprises an intra-operative registration module. In some embodiments, the system further comprises a corneal shield.

Aspects of the present disclosure include a method for treating an eye, the method comprising: generating a laser beam; splitting the laser beam into a pre-determined pattern with a diffractive optical element; and directing the patterned laser beam to a treatment zone of the eye, thereby treating a target issue in the treatment zone with the patterned laser beam. In some embodiments, the laser beam comprises a near-IR to mid-IR laser emission. In some embodiments, the laser comprises a wavelength range from about 500 nanometers (nm) to about 2 micrometers (μm). In some embodiments, the laser comprises a power from about 100 (milliwatts) mW to about 4 watts (W). In some embodiments, the laser comprises a pulse rep rate from about 1 hertz (Hz) to about 1000 Hz. In some embodiments, the treatment zone of the eye comprises the eyelids, sclera, retina, or any combination thereof. In some embodiments, the pre-determined pattern comprises an arcuate, annular, spotted, or line scan pattern. In some embodiments, the treatment may comprise a duration of from about 1 minute to about 30 minutes. In some embodiments, the treatment may comprise a treatment for dry eye, diplopia, convergence insufficiency, strabismus, or any combination thereof. In some embodiments, the method further comprises aligning the patterned laser beam to irradiate the treatment zone of the eye. In some embodiments, aligning comprises determining one or more optical signals on an alignment sensor. In some embodiments, the alignment sensor comprises a quad photo diode. In some embodiments, the one or more optical signals comprise one or more reflected optical signal from a cornea of a patient. In some embodiments, the one or more optical signals comprise near-infrared (NIR) illumination. In some embodiments, the near-infrared illumination comprises a wavelength range from about 850 nanometers (nm) to about 940 nm. In some embodiments, the method further comprises monitoring the laser beam power as the target tissue in the treatment zone is treated.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

DETAILED DESCRIPTION

Figure 1:
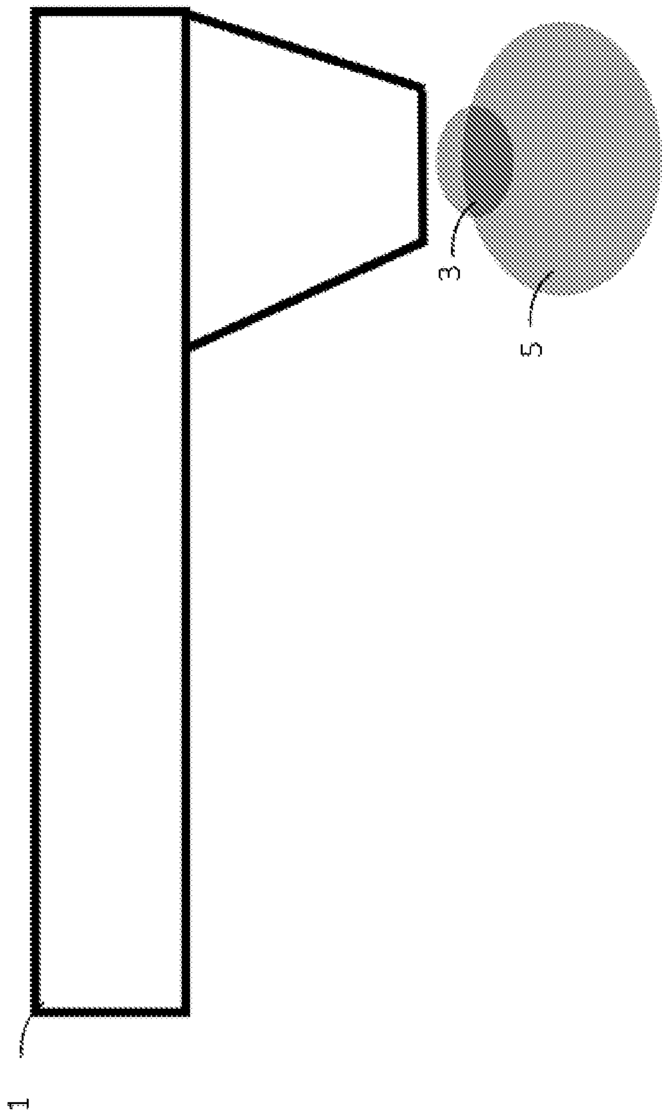
FIG. 1 shows a schematic view of a slit lamp adapted portable laser system for ocular therapy, in accordance with embodiments.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments, however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The present disclosure is described in relation to deployment of systems, devices, or methods for treatment of an eye of a patient. However, one of skill in the art will appreciate that this is not intended to be limiting and the devices and methods disclosed herein may be used in other anatomical areas and in other surgical procedures.

The embodiments disclosed herein can be combined in one or more of many ways to provide improved methods and apparatus for treating the eye. The treated ocular tissue, membranes, or pathological transformations thereof, may comprise one or more of sclera, retina, meibomian gland ducts, and diseased regions therein.

The embodiments as disclosed herein provide improved methods and apparatus for the treatment of one or more of dry eye disease, diplopia, convergence insufficiency, strabismus, glaucoma, and other ophthalmic conditions, or combinations thereof.

The present disclosure provides several unexpected advantages in view of current ocular treatment methodologies to treat glaucoma, presbyopia, dry eye, diplopia, convergence insufficiency, strabismus, retinal diseases, diabetic macular edema (DME), central serous retinopathy, retinal ganglion cell/pigment epithelium pathologies, Sirtuin3 modulation for cancer suppression, hydrogen peroxide suppression, macular telangiectasia, HSP and anti-oxidative upregulation, or any combination thereof. In some cases, the present disclosure may treat a thickened Bruch's membrane thereby reducing the thickness of the membrane. In particular, with regards to treating ocular refractive error (e.g., angular closure glaucoma), common techniques in the art rely on damaging or destroying cells in the eye that produce aqueous humor that may lend themselves to undesirable long-term side effects. Instead, the present disclosure provides a gentle yet effective treatment that precisely alters the hydraulic conductivity of the sclera thereby altering the angle formed by the cornea and iris. The present disclosure provides an unexpected result of treatment time compared to similar mechanisms of ocular laser therapy in that the device may treat a large field of view (e.g., an annular structure) rather than individually illuminating discrete field of view on the eye. This unique aspect of the present disclosure may also enable variable spatial treatment for complex ocular disease and/or conditions with variable spatial pathologies otherwise unattainable with devices understood by one of ordinary skill in the art. Additionally, the present disclosure describes a device that may comprise no moving parts that simplifies optical alignment of the device and cost of goods. The robustness of a design with no moving parts and low cost enables the widespread use of the device in resource limited regions of the world.

FIG. 1 shows an exemplary portable laser system 1 for ocular therapy. In some cases, the system 1 may treat the sclera 5 of an eye without causing injury to the iris, cornea 3, or other eye anatomical features posterior to the iris, e.g., pupil, lens, vitreous, retina, macula, optic nerve, or any combination thereof. The system may comprise a laser where the laser may comprise a near-IR to mid-IR laser (e.g., about 500 nm to about 2 μm), preferably a 0.515 um, 0.577 um, 0.690 um, 0.810 um, 1.44 μm to 1.56 μm laser. The laser may have a power within a range of about 100 mW to about 4 W. In some embodiments, one or more of the projected dimensions of the laser spot on the tissue may be within a range of about 0.2 mm to about 4 mm. For example, the laser may be a 2 W pulsed wave (PW) laser with a pulse rep rate within a range of about 1 Hz to about 1000 Hz. Alternatively, the laser may be a continuous wave (CW) laser within a power within a range of about 500 mW to about 1000 mW. The laser pattern delivery to the eye may be X-Y scanned or preferably Diffractive Optics generated over the target treatment tissue with a repetition rate within a range of about 1 Hz to about 1000 Hz.

The laser may be directed to treat a target ocular tissue (e.g., eyelids, sclera, retina) with a treatment pattern. The treatment pattern may include arcuate, annular, spotted, or line scans in selected sequences of multiple stacked or PW/CW laser regimes. The treatment pattern may be adjusted to obtain a desired degree of tissue de-calcification, translocation, shrinkage, microporation, vasodilation, thermal pulsation, and/or stimulation. For example, the laser may be directed to treatment zone on the target ocular tissue having a diameter within a range of about 1 mm to about 20 mm.

Figure 15:
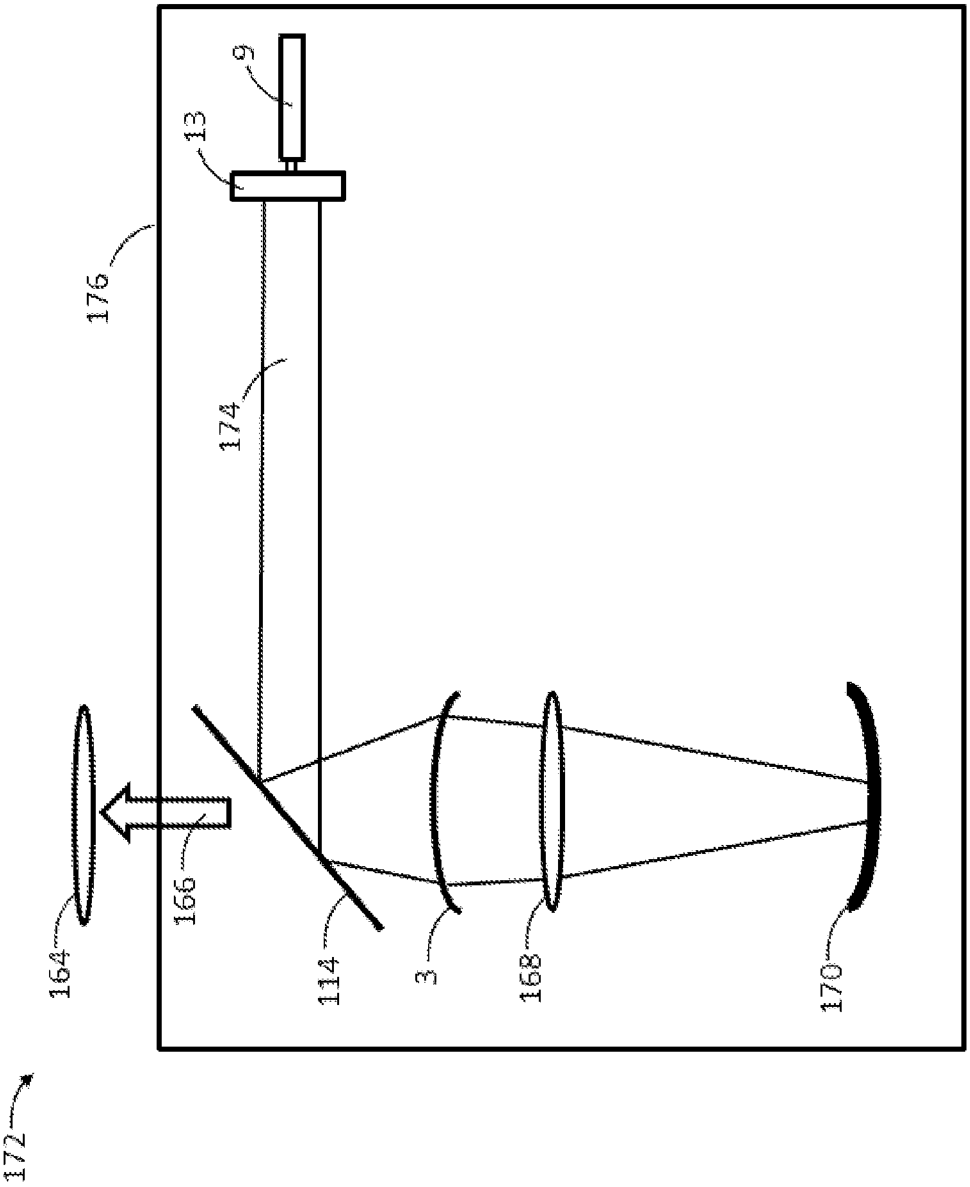
FIG. 15 shows a schematic of an embodiment of the devices disclosed herein to treat a patient's retina, in accordance with embodiments.

In some embodiments, the present disclosure describes a device 176 and system configuration 172 to treat retina tissue 170, as can be seen in FIG. 15. In some cases, the device 176 may comprise laser 9, diffractive optical element 13, mirror 114, or any combination thereof. In some cases, the mirror 114 may comprise a hot mirror, dichroic mirror, partially reflective mirror, or any combination thereof. In some cases, the device 176 may mechanically couple to a slit lamp system 164 that may enable the visualization of the patient's cornea 3, retina 170 or any combination thereof during a treatment procedure. In some instances, the mirror 114 may permit the slit lamp system 164 to visualize light 166 reflected from a patient's cornea 3, lens 168, retina 170, or any combination thereof during, before, or after a treatment. In some cases, the light reflective from a patients cornea 3, lens 168, retina 170, or any combination thereof, may comprise light in the UV, visible, near-infrared or any combination thereof spectra of light. In some instance, the diffractive optical element 13 may transform the input laser 9 light in a manner that produces a curved wave front emitted beam 174. In some cases, the curved focused wave front emitted beam 174 may treat a retina 170 of a patient. In some instances, the curved wave front of the curved wave front emitted beam 174 may produce better than expected results when treating a retina 170 of a patient due to the nature of the curved retina geometry. In some cases, the device may further comprise electronic circuitry comprising a processor and memory that may operably control the laser 9 and slit lamp system 164.

The device may be hand-held and aligned/registered to the eye with a contact patient interface device such as a cone with sensorized haptics or accessorized for Universal Slit Lamp Adaptation (Zeiss, Haag Streit, for example). The patient may be supine, recumbent, or upright.

The device may be configured to be handheld, or slit lamp adapted, with ease of surgeon control as the highest priority with the patient in a comfortable supine or recumbent or tilted or upright, slit lamp chair position. The laser may be battery-powered. Intraoperative user feedback provided may include power out of calibration, eye (de-)centration errors, left/right eye for example. Exemplary device may have hardware configured for Wi-Fi enabled cloud/internet communication and computing. In some cases, the Wi-Fi-enabled device may comprise an interface that may communicate with a server database informing the user or operator of the device payment/usage plan while using the device. In some instances, the billing rate may comprise a per use, subscription, or any combination thereof payment plan. In some cases, the Wi-Fi-enabled device may be configured to communicate with a server database to identify treatment parameters found to benefit patients of similar characteristics. In some cases, the characteristics may comprise the patient's age, gender, past medical history, history of present ocular condition, or any combination thereof.

Figure 12C:
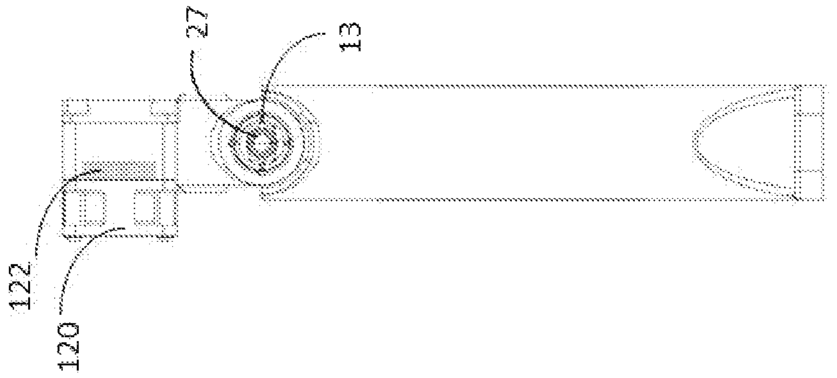
FIGS. 12A-12C show a side view (FIG. 12A), a side section view (FIG. 13B), and a front view (FIG. 12C) of a hand-held laser system for ocular therapy, in accordance with embodiments.
Figure 12B:
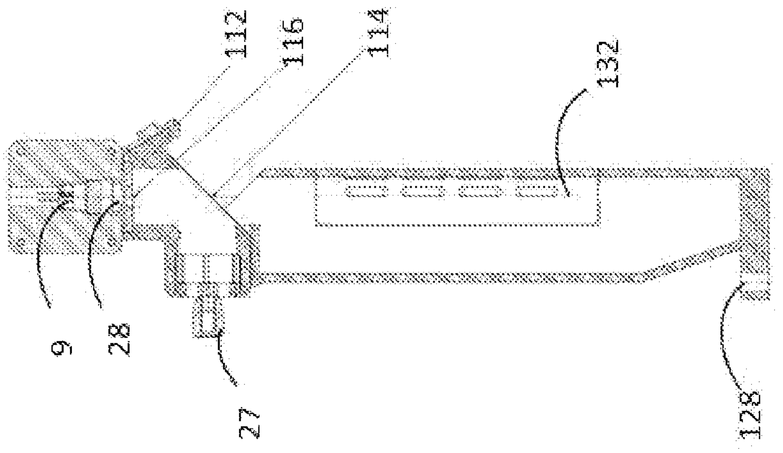
Figure 12A:
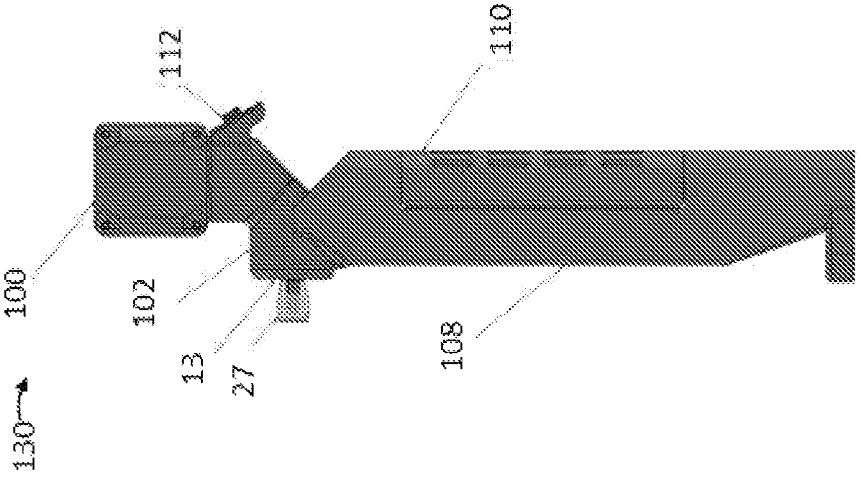

In some embodiments, the system may comprise a handheld device 130, as can be seen in FIGS. 12A-12C, that may be adapted to a conventional slit lamp or used handheld. In some instances, the device may comprise an illumination unit 100, visual guidance screen 112, optical relay 102, power source compartment 108, power source cover 110, diffractive optical element (DOE) 13, patient interface device (e.g., soft dock) 27, or any combination thereof as seen in FIG. 12A. In some cases, the diffractive optical element 13 may shape or direct the light source (e.g., laser) 9 such that the light source 9 after passing through the DOE may comprise a curved focal plane to match the curvature of a patient's cornea and/or retina. In some instances, the handheld device 130 may be configured to adapt to a conventional slit lamp through a mounting geometry 128, as seen in FIG. 12B. In some embodiments, the mounting geometry 128 may comprise a feature (e.g., a through hole) to fasten the device 130 to a structure of a conventional slit lamp using a machine screw. In some instances, the mounting geometry may couple with a surface of a conventional slit lamp through a tension press fit coupling. In some instances, the tension press fit coupling may comprise an interference fit between the device 130 and a dowel rod mechanically coupled to the conventional slit lamp.

In some cases, the power source compartment may comprise one or more batteries that may provide power to the handheld device 130. In some cases, the power source compartment 108 may comprise an analog current (AC) to direct current (DC) converter, configured to electrically couple to a standard wall electrical socket. The analog current AC to DC converter may operate at a voltage of about 120 volts (V) to 240V. In some instances, power source compartment 108 may be mechanically coupled to a power source cover 110, that may provide ventilation to the one or more batteries, the AC to DC converter, circuitry of the device described elsewhere herein, or any combination thereof.

In some instances, the illumination unit 100 may comprise a light source 9, wherein the light source may comprise a light emitting diode (LED), super-luminescent diode (SLD), pulsed laser, pulsed diode laser, continuous wave laser, or any combination thereof. In some instances, the light source may comprise one or more optical elements 28, that may shape or modify the path of one or more emitted beams of the light source. In some instances, the one or more optical elements 28, may comprise one or more plano-convex, bi-convex, plano-concave, or bi-concave lenses. In some cases, the one or more optical elements 28, may be configured to collimate or focus the one or more emitted beams of the light source 9 to a collimated or parallel beam. In some cases, the illumination unit may be coupled to a fan 120, as can be seen in FIG. 12C configured to provide a cooling convective flow to maintain the stability and output of the light source. In some instances, the fan 120 may be thermally coupled to a heat sink 122, configured to distribute and/or dissipate the heat generated by the light source 9.

In some instances, the visual guidance screen 112 may comprise an organic light-emitting diode (OLED), LED, or any combination thereof display configured to display device settings and parameters. In some cases, the visual guidance screen 112 may comprise a touch screen interface allowing a user or operator to interact with different menus. In some cases, the visual guidance screen 112 may comprise an interface that allows a user or operator to select, adjust, save, or any combination thereof actions completed on the device. In some instances, the visual guidance screen 112 may comprise a menu and/or user interface configured to enable treatment. In some instances, the visual guidance screen 112 may comprise a menu and/or user interface displaying the treatment time elapsed, treatment parameters, or any combination thereof. In some cases, the visual guidance screen may comprise one or more LEDs. In some cases, the one or more LEDS may emit a one or more bandwidths of light from about 400 nanometers (nm) to about 700 nm.

In some instances, the handheld device 130, may comprise an optical relay 102. In some cases, the optical relay may comprise a mirror 114. In some instances, the mirror 114 may be a hot mirror, dichroic mirror, partially reflective mirror, or any combination thereof. In some instances, the mirror 114 may be configured to alter the path of the one or more emitted beams generated by the light source 9, allowing the transmission of one or more bandwidths of light to a user or operator. In some instances, the mirror 114, may transmit light with a bandwidth in the visible, and/or near-infrared spectra. The visible spectra may comprise wavelengths of light from about 400 nm to about 800 nm. In some instances, the near-infrared spectra of light may comprise wavelengths of light from about 900 nm to about 1500 nm. In some cases, the mirror 114 may be configured to optically coupled to an optical illumination and/or visualization system of a conventional slit lamp.

In some cases, the mirror 114 may be configured to reflect light in a near infrared (NIR) spectrum yet transmit light of the visible spectrum. In some instances, the mirror 114 may provide a patient eye/docking view that may provide visualization of the treatment pattern incident on the patient's eye. In some cases, the mirror 114 may comprise one or more indicators. In some instances, the indicators may comprise a waveguide feature configured to illuminate a status indicator color (e.g., red, green blue, yellow, etc.). In some instances, the mirror 114 may comprise an LED or LCD display that may provide visual information to an operator or user regarding device treatment status, e.g., duration of treatment elapsed, light source emission status, or any combination thereof.

In some cases, the diffractive optical element 13 may comprise one or more optical elements in optical communication with the one or more emitted beams of light. In some cases, the one or more optical elements may be arranged to generate a treatment pattern. In some cases, the one or more optical elements may be configured to sense and/or measure a calibration power of the light source. In some instances, the treatment pattern may comprise an arcuate, annular, spotted, linear, or any combination thereof illumination geometry.

In some instances, the hand-held device may comprise a patient interface device 27 (e.g., a soft dock), configured to mechanically couple to the patients cornea thereby stabilizing the patient's eye with respect to the device and vice versa. In some cases, the soft dock may comprise a semi-rigid and/or compressible material. In some cases, the material may comprise a silicon-based material, an FDA approved biocompatible plastic, or any combination thereof. In some instances, the soft dock may comprise an eye alignment system, described elsewhere herein. In some cases, the soft dock may be disposable, sterilizable, or any combination thereof.

The eye of the patient may be fixed using conventional techniques as will be understood by one of ordinary skill in the art such as contralateral eye, cone capture, eye tracker, or any combination thereof eye fixing approaches described in some embodiments.

Any of the systems described herein may include a patient interface in order to provide beneficial outcomes such as a fixed working distance, pre-treatment and/or intra-operative registration/alignment (e.g., cross-hair) and fixation (e.g., suction), haptics for greater margin of safety (e.g., origami folds, spring loaded, differential elasticity segments), speculum functionality to hold eyelids open, sterility (e.g., shape/material), soft-dock for patient comfort (e.g., elastic interface contact lens), and/or corneal protection from laser exposure (e.g., carbonized contact lens), among others.

Therapy (e.g., surgery) preparation may entail eye drops, such as trehalose and other analgesic (lidocaine etc.) medications, as well as protective contact lenses speculum, as will be understood by one of ordinary skill in the art.

The duration of therapy may vary from about 1 minute to about 30 minutes. In some embodiments, the duration of therapy may be more than 30 minutes. Open eye treatments may be under 5 minutes, preferably under 2 minutes, while closed eyelid treatments may be up to 15 minutes, preferably under 5 minutes.

In some embodiments, the surgeon hand-held laser (NIR/mid-IR) can be suctioned onto a cornea, with compliant Z-elasticity (haptic) but XY rigidity, and annulus diameter, spot diameter, pulse rep frequency, pulse width, number of pulses, and/or power may be pre-settable.

Treatment times for drug delivery, muscle translocation, de-claudication glaucoma treatments may be about 10-60 secs per annulus.

Power range 2 Watts, PRF range 1 kHz, annular spots or rings or arcs are feasible, with laser wavelengths of 0.529 um, 0.810 um, 1.47 um, 1.56 um, 2.01 um being preferred.

In some embodiments, the system may comprise a laser scanner for illuminating (i.e., printing) directly on a surface of a patient's eye.

In some embodiments, the system may comprise a laser scanner for printing over a patient's closed palpebrae (eyelids). A camera may be included in some embodiments for closed eye checks and shape extraction for custom delivery with intraoperative progress monitoring. Eyelid areas including subsets of up to 20 mm diameter can be scanned.

In some embodiments, such as for dry eye disease therapy, the mid-IR laser can be scanned over eyelids to heat underlid temperature to 38 C, while the upper eyelid does not exceed 44 C. Preferably, the underlid temperature may be heated to about 37 C, while the upper eyelid does not exceed 40 C. The duration of therapy may vary from 1 to 30 minutes. The outer lid surface may be protected by mid-IR-transparent thermally-conductive sprays and/or devices (e.g., similar to a motorized toothbrush and water).

Figures 2, 3:
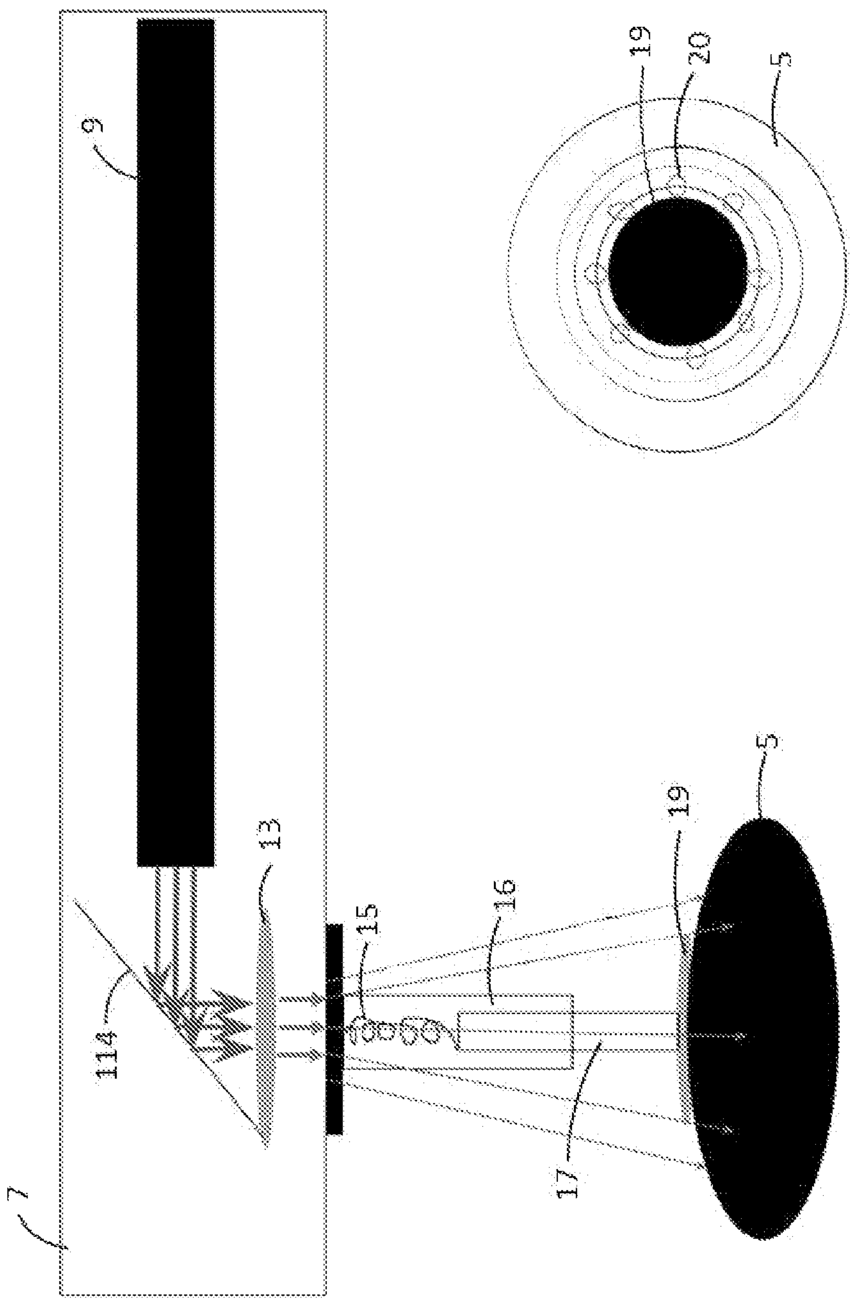
FIG. 2 shows a side schematic view of a slit lamp adapted portable laser system for ocular therapy, in accordance with embodiments.
FIG. 3 shows a top view of an eye showing an exemplary treatment pattern using the system of FIG. 2, in accordance with embodiments.

FIG. 2 shows a portable laser system 7 for ocular therapy. The system 7 may be substantially similar to the system of FIG. 1 except that the laser may be projected over the target treatment tissue in a treatment pattern. The laser 9 may comprise a mid-IR laser (e.g., about 800 nm to about 2 μm), preferably a 1.45 μm to 1.56 μm laser. The laser may have a power within a range of about 100 mW to about 2 W. The laser 9 may have a spot size diameter within a range of about 0.2 mm to about 1 mm. For example, the laser may be a 2 W PW laser with a pulse rep rate within a range of about 1 Hz to about 1000 Hz. Alternatively, the laser may be a CW laser with a power within a range of about 500 mW to about 1000 mW. A laser treatment pattern (e.g., annulus, spotted annulus, etc.) may be projected over the target treatment tissue with a repetition rate within a range of about 1 Hz to about 1000 Hz. The laser 9 may emit a beam of light that may be steered or modified by one or more optical elements. In some cases, the emitted beam of light of the laser 9 may be reflected, refracted, diffracted, or any combination thereof interaction with a mirror 114.

The laser may, for example, be projected over the target treatment tissue using one or more diffractive optical elements 13. The diffractive optical element 13 may comprise fused silica glass when used with mid-IR laser wavelengths. The diffractive optical elements may be configured to project annuli, arcs, and/or spots onto the sclera, eyelids, limbus, and/or muscle insertions for treatment. The diffractive optical elements 13 may project any pattern, shape, or number of spots desired. For example, the diffractive optical element may project a 40-spot annular pattern onto a target treatment zone of the eye. In some instances, the zero-order spot (e.g., the central spot on the cornea) may be blocked by a suction ring 19. In some cases, the suction ring may mechanically couple to a suction rigid member 17 that may further mechanically couple to a spring 15. In some cases, the suction rigid member 17 may interface with a suction channel 16 that may provide controlled linear translation of the suction rigid member 17 towards and away from the sclera 5 of a patient. In some cases, the spring may comprise a spring coefficient configured for maintaining suction of the suction ring 19 over a patient's cornea.

The laser 9 may be directed to treat a target ocular tissue (e.g., eyelids, sclera, retina) with a treatment pattern. The treatment pattern may include arcuate, annular, spotted 20, or lines in selected sequences of multiple stacked or PW/CW laser regimes. The treatment pattern may be adjusted to obtain a desired degree of tissue translocation, shrinkage, microporation, vasodilation, thermal pulsation, and/or stimulation. For example, the laser may be directed to a treatment zone on the target ocular tissue having a diameter within a range of about 1 mm to about 20 mm.

The device may be handheld and aligned/registered to the eye with a contact patient interface device (15, 17, and 19) such as a cone with haptics or slit lamp adaptor. The patient may be supine, recumbent, or upright.

The device may be configured to be handheld, slit lamp adapted, with ease of surgeon control as the highest priority with the patient in a comfortable supine or recumbent or tilted chair position. The laser may be battery-powered.

The duration of therapy may vary from about 1 minute to about 30 minutes. In some embodiments, the duration of therapy may be more than 30 minutes. Open eye treatments may be under 5 minutes, preferably under 2 minutes, while closed eyelid treatments may be up to 15 minutes, preferably under 5 minutes.

In some embodiments, the surgeon hand-held laser (IR/mid-IR) can be suctioned onto a cornea, with compliant Z-elasticity (haptic) but XY rigidity, and annulus diameter, spot diameter, pulse repetition frequency (PRF), pulse width, number of pulses, and/or power may be pre-settable.

Treatment times for drug delivery, muscle translocation, de-claudication glaucoma treatments may be about 10-60 seconds per annulus.

Power range 2 Watts, PRF range 1 kHz, annular spots or rings or arcs are feasible, with laser wavelengths of 0.515 μm, 0.810 μm, 1.45 μm, 1.56 μm, 1.9 um, or 2.01 μm being preferred.

In some embodiments, the system may comprise a laser with a diffractive optical element for projecting onto a patient's closed palpebrae (eyelids). A camera may be included in some embodiments for closed eye checks and shape extraction for custom delivery with intraoperative progress monitoring. Eyelid areas including subsets of up to 20 mm diameter can be scanned.

In some embodiments, such as for dry eye disease therapy, the mid-IR laser can be projected over eyelids to heat underlid temperature to 38 C, while the upper eyelid does not exceed 44 C. Preferably, the underlid temperature may be heated to about 37 C, while the upper eyelid does not exceed 40 C. The duration of therapy may vary from 1 to 30 minutes. The outer lid surface may be protected by mid-IR-transparent thermally-conductive sprays and/or devices (e.g., similar to a motorized toothbrush and water).

FIG. 3 shows a top view of an eye showing an exemplary treatment pattern 20 using the system of FIG. 2. The diffractive optical element may be configured to project three annuli, each comprising an array of spots 20, onto the sclera 5 of the eye. A corneal shield (e.g., mid-IR opaque contact lens) may be disposed over the cornea to prevent undesired exposure thereto.

Indications which may be treated using the systems, methods, and apparatus described herein include dry eye (e.g., meibomian gland opening via thermal pulsation with a laser scanned or projected on closed eyelids), diplopia (e.g., via customized translocation of extra-orbital muscle insertion zone with open eye treatment), convergence insufficiency (e.g., via customized translocation of extra orbital muscle insertion zone with open eye treatment), and strabismus (e.g., via customized translocation of extra orbital muscle insertion zone with open eye treatment). Alternatively, or in combination, the systems, methods, and apparatus described herein may be used for laser-enhanced ocular drug delivery to the sclera or other ocular tissues. Therapeutics such as anti-VEGF agents, glaucoma medications, and other medicaments can rapidly permeate ocular tissues with laser-based drug delivery treatments. In some embodiments, the systems, methods, and apparatus described herein may be used to treat monovision.

In some embodiments, the systems, methods, and apparatus described herein may be used for treatment of primary open angle glaucoma (POAG) and/or primary angle closure glaucoma (PACG). For example, the systems, methods, and apparatus described herein may be used for transscleral delivery of near- to mid-IR laser energy under a topical anesthetic (optionally without using a slit lamp). Treatment duration may be about one minute per eye for either closed angle or open angle glaucoma. The laser may be an 810 nm laser (e.g., near-IR), or a mid-IR laser (e.g., within a range of about 1.4 μm to 1.6 μm). Treatments may be patterned to rotate the scleral spur (ACG), curtail aqueous secretion (CP), decalcify exposed regions of eye tissue, dilate Schlemm's Canal/Trabecular Meshwork/Collector Channel cross sectional areas, and/or increase uveoscleral outflow/hydraulic conductivity by induced scleral softening.

Corneal treatments for hyperopia, astigmatism and spherical aberration can be configured at 810 nm, 1.4 μm to 1.6 μm, and other IR wavelengths (1.9 μm, 2.01 μm for example).

Any of the systems described herein may be used to treat a patient in a supine or recumbent position.

In some embodiments, the portable laser system may be battery-powered and/or rechargeable.

Figure 4B:
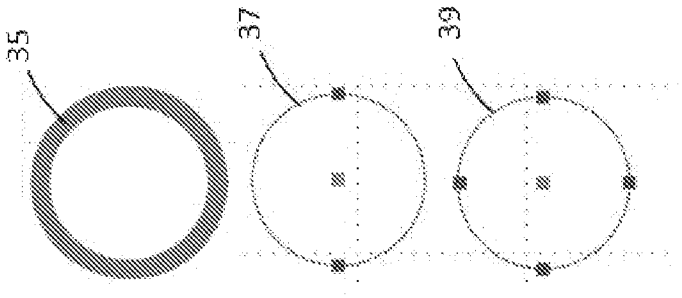
FIGS. 4A-4B show a side section view of a portable laser system in use for ocular therapy including a patient interface (FIG. 4A) and a front view of an annular projection provided by the portable laser system (FIG. 4B), in accordance with embodiments.
Figure 4A:
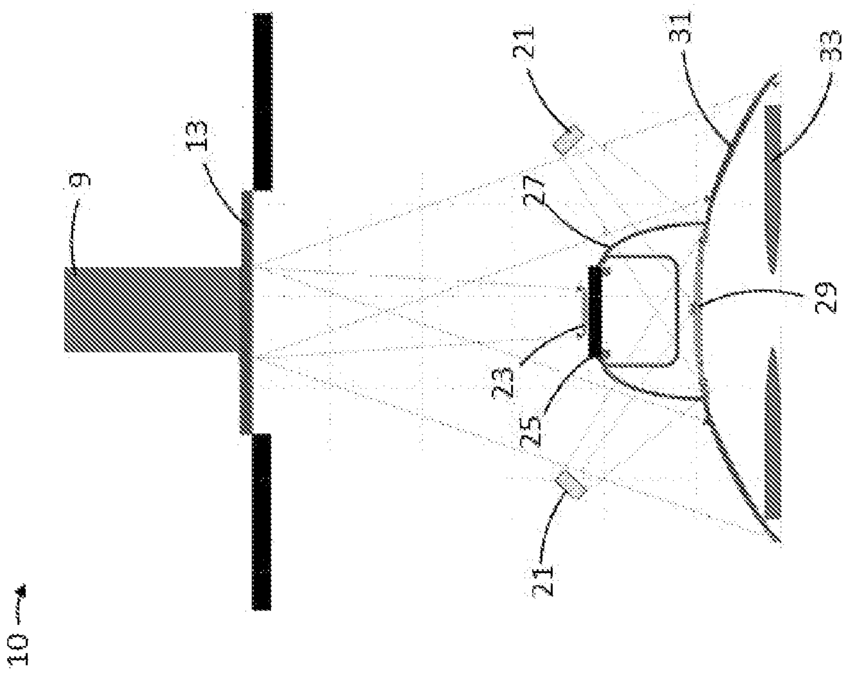
Figure 11:
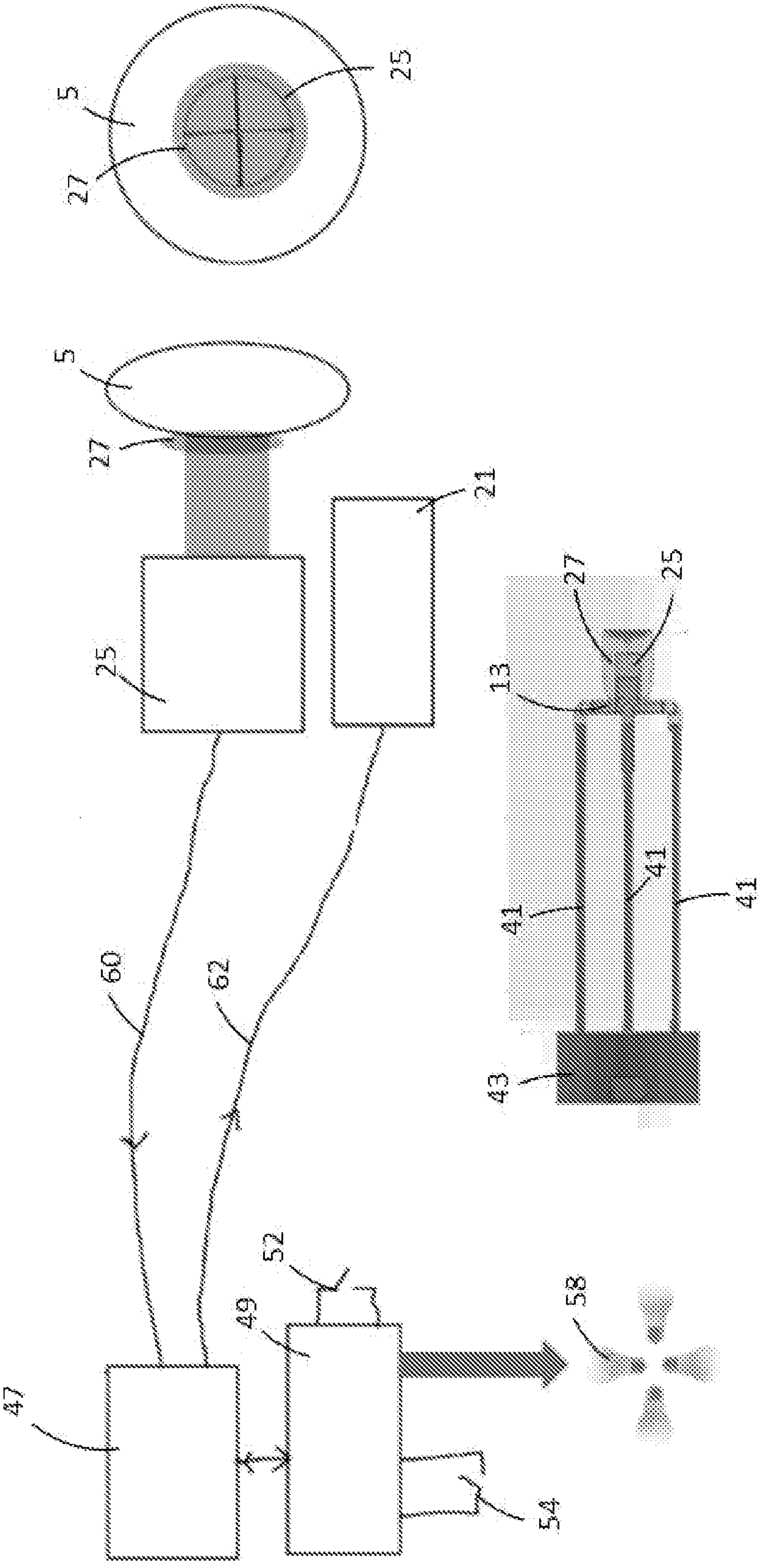
FIG. 11 shows a schematic of docking system sensors, in accordance with embodiments.

FIGS. 4A-4B show a portable laser system 10 for ocular therapy including a patient interface. The system may comprise a portable (e.g., battery-powered) light source 9, e.g., a diode laser coupled to a diffractive optical element (DOE) 13 for targeting energy deposition on ocular treatment zones on the patient's sclera 31. The portable laser system may comprise any of the lasers described herein. The portable laser system may comprise any of the diffractive optical elements described herein. Patient interface device 27 (such as a docking system as described herein) may precisely couple the laser aperture to the treatment eye at a fixed working distance. The docking system adaptors may be configured to point, stabilize, and/or couple sensors located near the point of eye contact (e.g., at the patient interface). A laser power sensor 23 (e.g., an InGaAs sensor) may be configured to measure the central laser diffractive optical element beamlet ("zero order") directed towards the cornea 29. A quad photodiode 25 may sample in quadrants (e.g., X+/−, Y+/− as shown in FIG. 11) near-IR LED 21 illumination reflected from the treatment eye (iris 33/pupil)

through a pinhole. Current mirrors, transconductance amplifiers, and filters with microprocessors may condition the photodiode sensor signals. Software may detect, analyze, and/or provide real-time surgeon feedback, for example: no eye contact or eye contact but motion occurred, with automatic treatment pause/shut-off. A laser power 23 sensor may calibrate the laser pre-treat start and may optionally continuously monitor laser power during treatment. Near-IR LED pupillary illumination 21 may be directed through an eye contact diffuser interface, so movement or slippage in eye position during treatment may vary quad photodiode 25 currents monitored by microprocessor in real time. Optionally, corneal suction may be modulated via a patient interface device 27 in a control loop when analyzing eye-slip monitoring via quad photodiode currents.

The diffractive optical element/laser aperture may be located about 100 mm from the treatment eye. The diffractive optical element may project a, annulus 35 (e.g., about 12 mm-18 mm diameter annulus) onto the sclera with the input laser beam characteristics for a VIS/near-IR/mid-NIR wavelength as described herein, as seen in FIG. 4B. In some cases, the treatment pattern may comprise one or more spots of illumination 37, 39. Lower/higher orders of diffractive optical elements may be blocked, for example to restrict the light pattern from damaging the cornea 29 and interacting with the iris 33 potentially damaging the iris 33 or any other anatomical features posterior to the iris. Patterns such as arcs, octal-, quad-, and dual-spot patterns may be user-selectable. The relative power delivered in the treatment zone may be over 50% (e.g., a 2-Watt laser may deliver about 1 Watt in the annulus on the sclera). A key novel feature is that no moving parts (such as scanners, manual laser beam motion control) are required for treatments with this configuration resulting is significant ease of use and low cost.

The patient interface device 27 on the cornea may be a sterile disposable feature configured to transmit near-IR illumination (e.g., about 850 nm) towards the cornea/iris, with resulting diffuse iris/pupil-reflected near IR spot landing inside the sensitive quad photodiodes via a pinhole. In some embodiments, the portable device may have one, two, or three patient contacts (e.g., head rest, nose bridge, and corneal applanation) for stable laser delivery. Slit lamp adaptor use may be realized in some embodiments.

The hand-held portable laser system may weigh about 750 gms and use low-cost parts to reduce overall system costs. The system may be microprocessor-controlled with display and have optional wavelengths selectable from near-IR to mid-IR, with up to 4 Watts output in pulsed and continuous wave modes for at least 8 treatments per charge.

Figure 5:
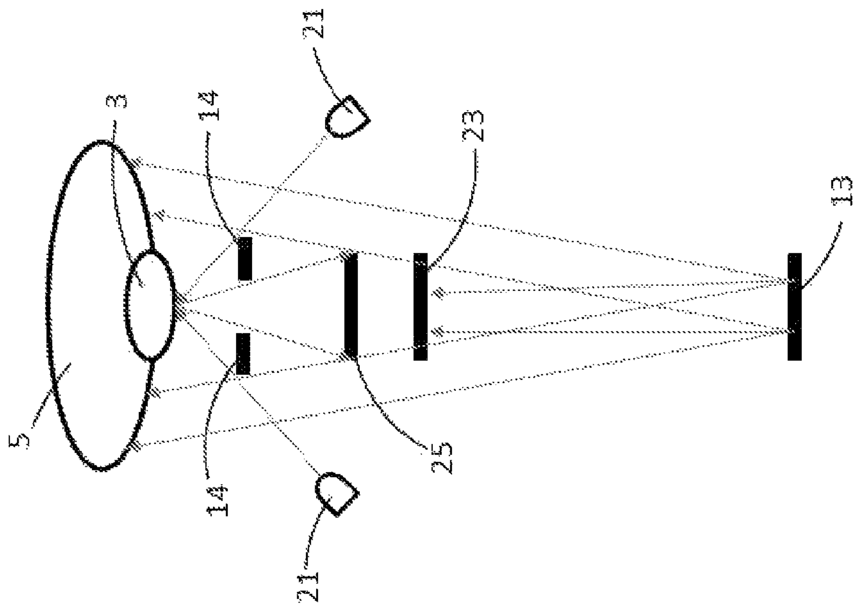
FIG. 5 shows a light path schematic of a portable laser system for ocular therapy, in accordance with embodiments.

FIG. 5 shows a light path schematic of a portable laser system for ocular therapy. The portable laser system may be substantially similar to the system shown in FIG. 4, including a portable laser, a diffractive optical element 13, pin hole 14, a patient interface comprising a soft disposable contact lens, laser power sensor, docking system sensor 25, a fixed-working distance docking system, or any combination thereof. In some cases, the pin hole 14 may limit the reflected NIR pupillary illumination LED 21 light off of the iris directed towards the docking system sensor 25. In some cases, by adjusting the size of the pinhole 14 the detectable range of rotational motion of the iris center of mass may be achieved. In some cases, the size of pin hole 14 may be set to detect 2 mm range of rotational motion of an iris. The system may include laser power calibration and self-check using one or more sensors (23, 25) as described herein. The system may include eye position feedback and/or slip-motion monitoring as described herein. The system may include OD/OS auto-detection.

Figure 6:
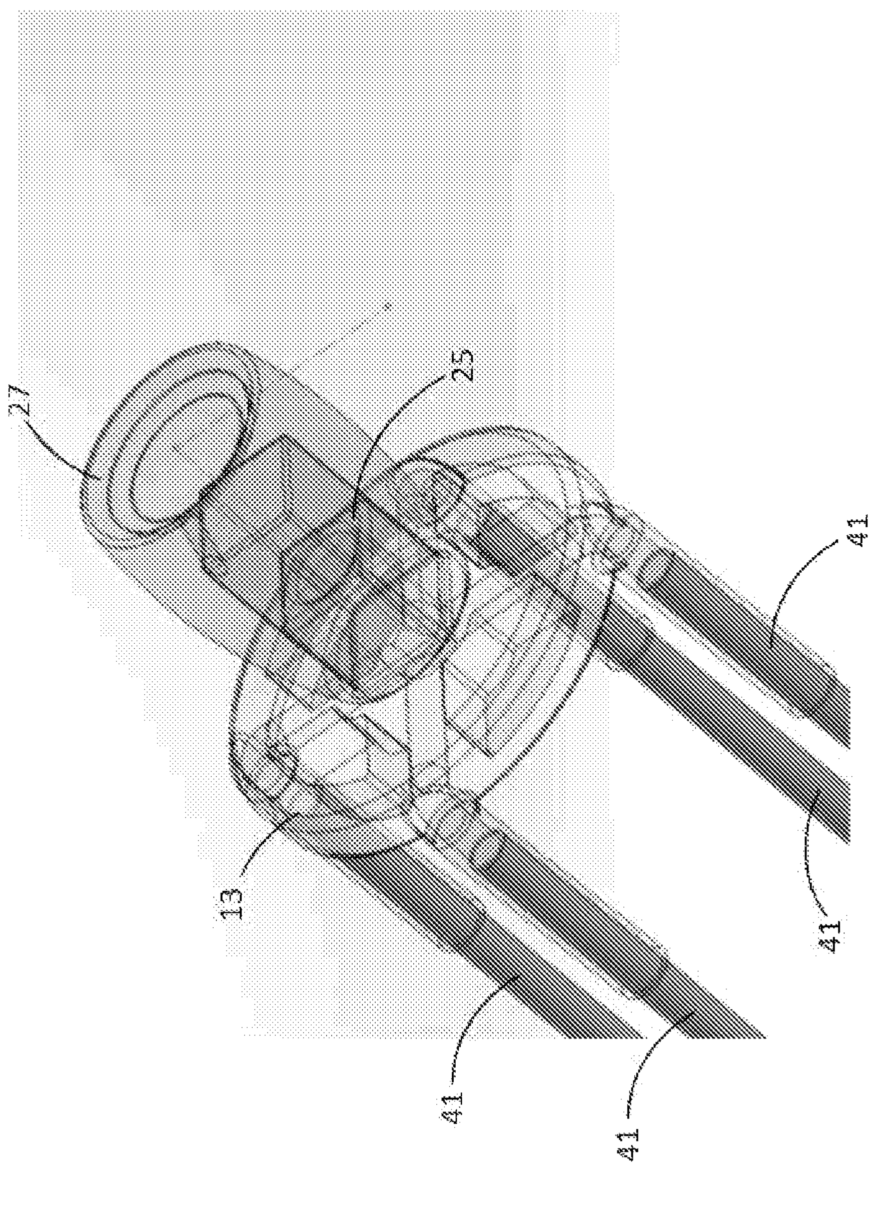
FIGS. 6-9 show a magnified perspective view (FIG. 6), a side section view (FIG. 7), perspective section view (FIG. 8), and front view (FIG. 9B) of a patient interface and portable laser docking system, in accordance with embodiments.

FIGS. 6-9 show various views of a patient interface and portable laser docking system 42. FIG. 6 shows a perspective view of the distal (i.e., eye-contacting) end of the patient interface device 27, with a proximal end of the patient interface being coupled to distal end of a laser docking system 42. The patient interface and portable laser docking system 42 may be used in any of the portable laser systems described herein. The patient interface may comprise a square extension 13 coupled to a disposable patient interface device (PID) 27 comprising suction channels/ports to secure the PID to the surface of the eye. The disposable PID 27 may comprise an IR-translucent diffuser. A central portion of the contact lens and/or square extension 13 (e.g., about 10 mm diameter) may be configured to block incoming laser light and protect the cornea from errant laser energy (e.g., unwanted "zero order" laser energy emanating from the diffractive optical element). In some embodiments, the central blocking element may include a sensor 25 configured to calibrate the laser and/or monitor the power of the laser. In some embodiments, the central blocking element may include quad photodiodes configured to monitor eye position and movement as described herein. The patient interface device 27 may be coupled to the docking system at a circular mount 13 of the docking system. The circular mount may comprise channels for wiring (e.g., for various sensors as described herein) and/or stainless-steel tube insertion 41.

Figure 7:
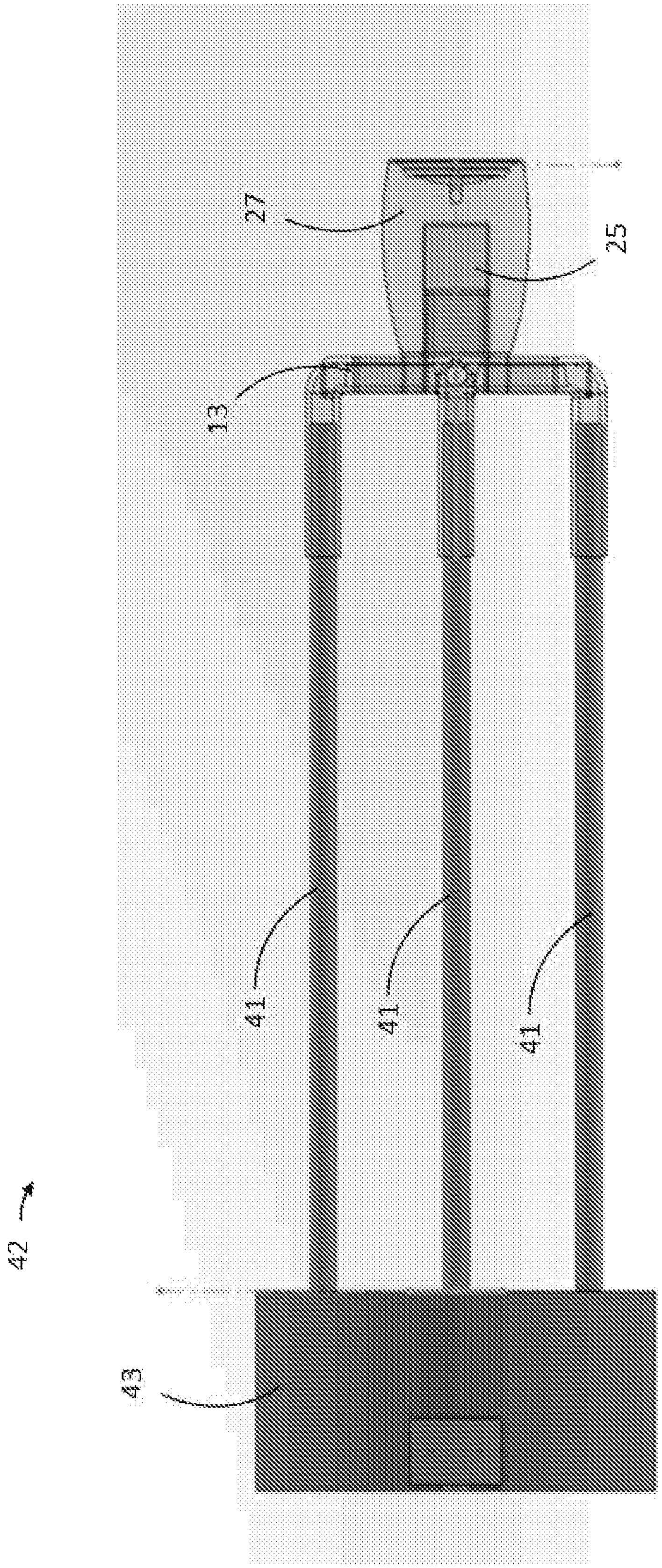

FIG. 7 shows a side view of the patient interface and docking system 42. In some embodiments, the docking system may comprise a plurality of stainless-steel tubes 41 coupled to matching laser head holes disposed on a proximal end 43 thereof. The stainless-steel tubes 41 may provide a fixed working distance between the portable laser and the eye. In some embodiments, the tubes may be about 8 cm long. In some embodiments, the tubes may provide a path for the laser energy to travel between the diffractive optical element and the eye.

In some embodiments, the docking system may comprise an XY quad sensor (e.g., as shown in FIG. 11) for motion detection.

Figure 8:
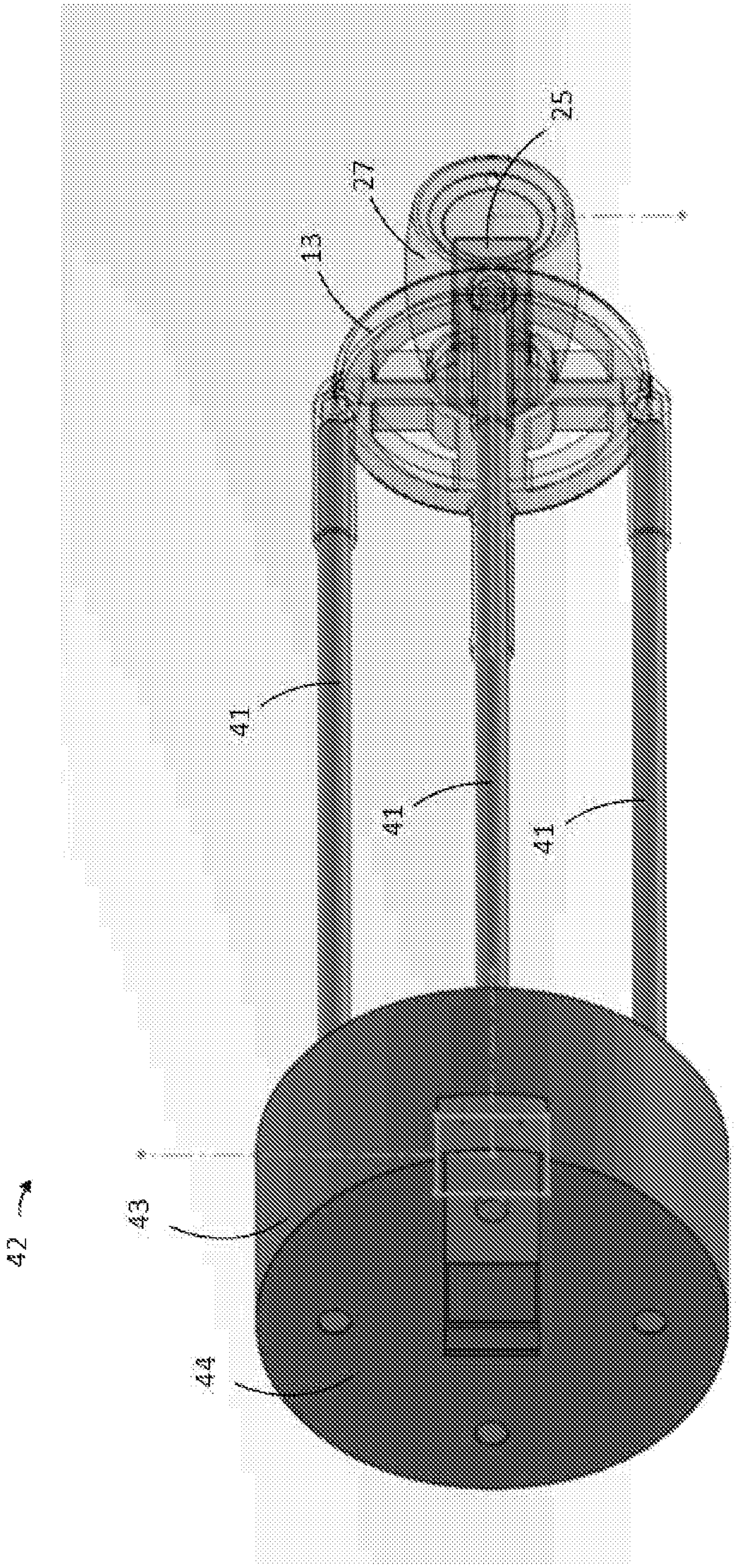

FIG. 8 shows a perspective view of the proximal end 43 of the docking system. The proximal end of the docking system may include an input 44 for the laser diode and/or laser beam of the portable laser system. The proximal end of the docking system may comprise a diffractive optical element and/or may be coupled to a selectable/adjustable diffractive optical element (e.g., via a latch, etc.).

In some embodiments, the system may include a headrest in addition to the docking system/patient interface described herein.

Figure 10:
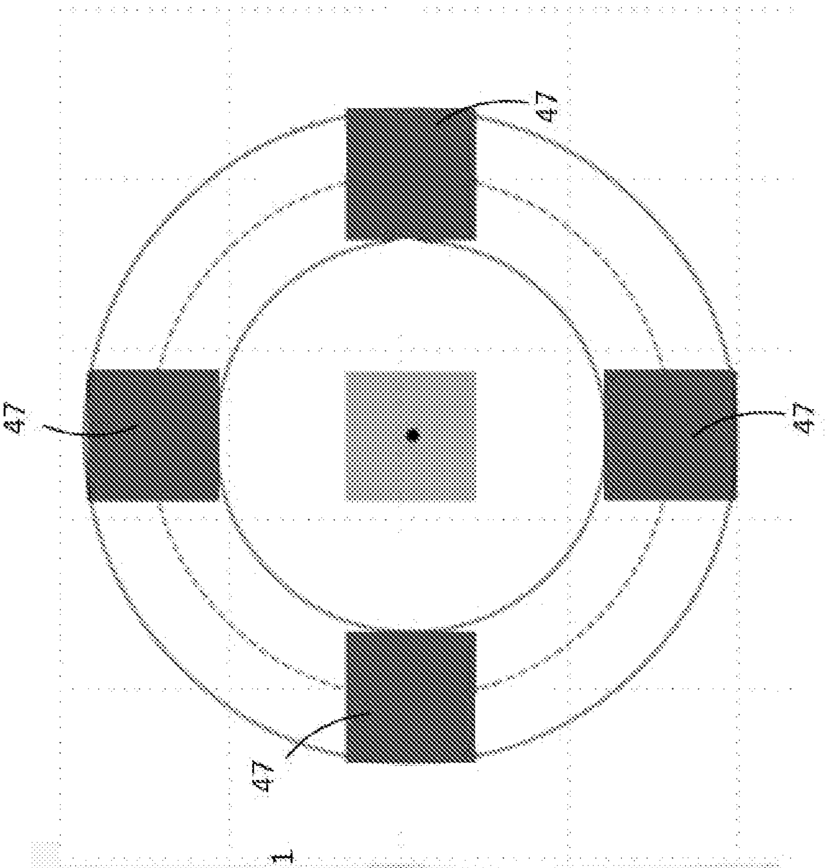
FIG. 10 shows a front view of an exemplary treatment pattern, in accordance with embodiments.
Figure 9:
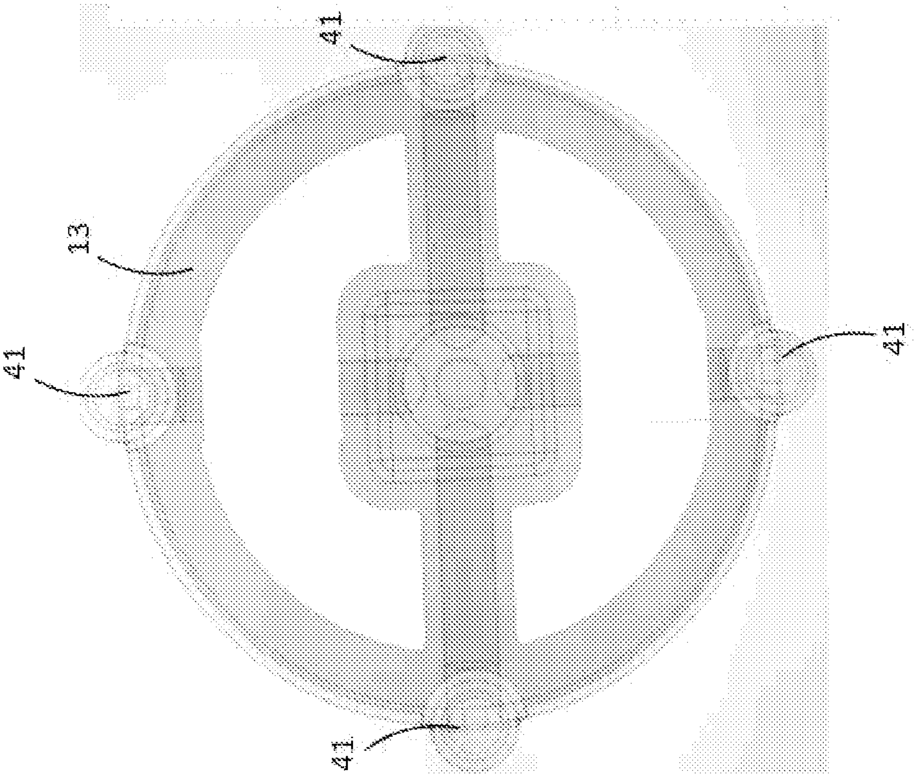

FIG. 9 shows a planar view of the distal end of the patient interface and docking system 42. FIG. 10 shows an exemplary treatment pattern. The patient interface and laser docking system shown 42 in FIGS. 6-9, for example, may be used to generate a laser treatment pattern on the eye. The treatment pattern may, for example, include four treatment spots 47, one per quadrant of the eye, at a pre-determined radial distance from the center of the eye (e.g., 12 mm to 20 mm from the center of the eye).

FIG. 11 shows a system schematic and wire diagram of how the docking system sensor 25, laser source 9, microcontroller 49, optical signal processor 47, Near-IR LED pupillary illumination 21, status indicator 58, and patient interface and portable laser docking system 42 may interface and communicate with one another. In some cases, the docking system sensor 25 may be used to monitor eye-slippage and/or docked position of the patient interface on the eye. NIR LED (e.g., with illumination LEDs at about 850 nm to about 940 nm) pupillary illumination 21 may be directed through a patient interface device 27. In some cases, the pupillary illumination 21 may be enabled by an optical processor 47. Movement and/or slippage in eye position during treatment may vary quad photodiode 25 currents, thereby detectable as a change in electrical signal (e.g., current and/or voltage) 60 monitored by microprocessor 49 and optical processor 47 in real time (e.g., greater than at least about 30 Hz). Movement and/or slippage of the eye may trigger a status indicator 52 to alert the physician, user, and/or operator (e.g., a status indicator 58) and/or stop treatment 54 and require repositioning of the patient interface and/or docking system before treatment can resume. In some embodiments, the system may be coupled to a footswitch to allow the physician to pause treatment, etc., e.g., when movement is detected. Laser parameters similar to conventional laser therapy can be efficiently delivered in a user-friendly manner with the laser systems and methods described herein.

Figure 14:
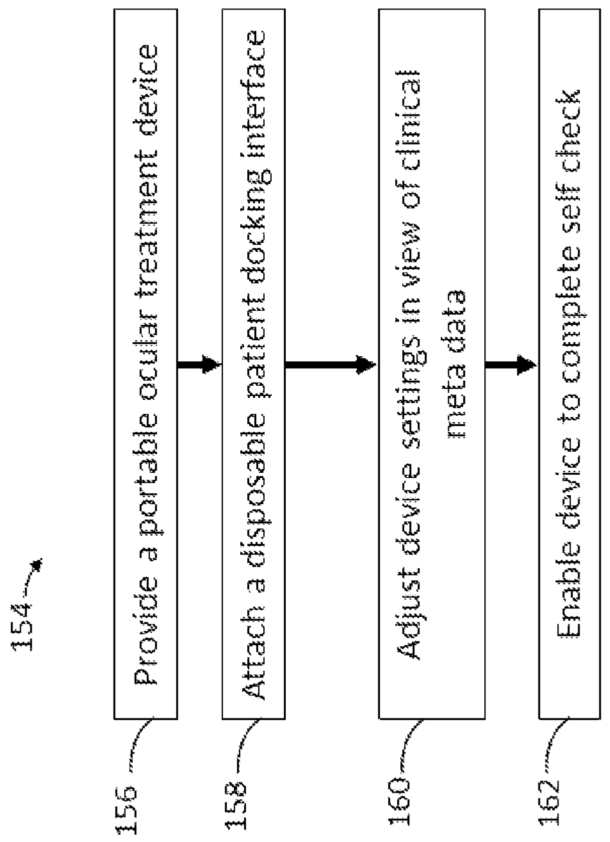
FIG. 14 shows a workflow diagram for configuring the devices of the invention prior to treating a patient, in accordance with embodiments.

In some embodiments, the disclosure provided herein may comprise a method 154, as seen in FIG. 14, of configuring a portable laser system for ocular therapy. In some cases, the method 154 may comprise the steps of: (a) providing a portable ocular treatment device 156; (b) attaching a disposable patient docking interface 158; (c) adjusting the portable laser system settings in view of the clinical meta data 160; and (d) enabling the device to complete a self-check 162. In some instances, the disposable patient docking interface may comprise a silicon material, as described elsewhere herein. In some cases, the docking interface may be sterilizable. In some instances, the portable ocular treatment device may be mechanically in communication with a slit lamp device. In some cases, the clinical meta data may comprise patient age, gender, past medical history, current ocular treatment treated, or any combination thereof. In some cases, the device self-check may comprise detecting or sensing the laser source output at a laser power detector. In some cases, the laser power detector may determine if the laser power detected is within a range of acceptable laser power based on manufacture specifications.

Figure 13:
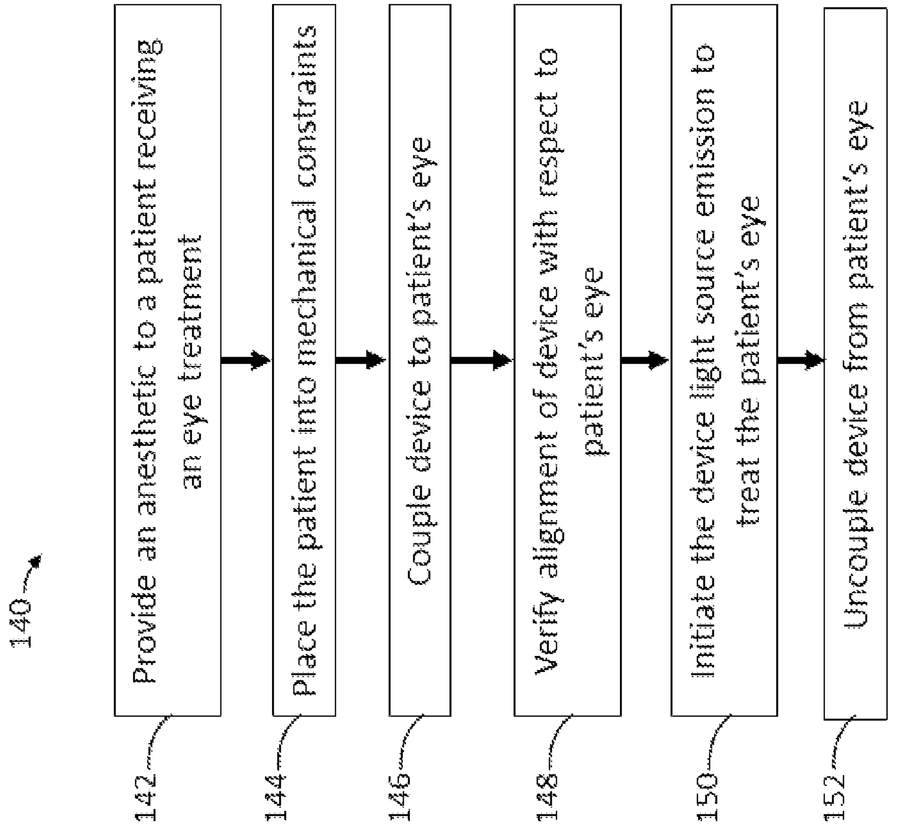
FIG. 13 shows a workflow diagram for a method of treating a patient using a portable laser system for ocular therapy, in accordance with embodiments.

In some embodiments, the disclosure provided herein may comprise a method 140, as seen in FIG. 13, of treating an ocular condition (described elsewhere herein) with a device (described elsewhere herein) of one or more patients at a point of care, emergency hospital setting, surgical theater, outpatient clinic, medical office, or any combination thereof settings. In some instances, the ocular conditions treated by the device may comprise, but are not limited to, dry eye (e.g., meibomian gland opening via thermal pulsation with a laser scanned or projected on closed eyelids), diplopia (e.g., via customized translocation of extra-orbital muscle insertion zone with open eye treatment), convergence insufficiency (e.g., via customized translocation of extra orbital muscle insertion zone with open eye treatment), strabismus (e.g., via customized translocation of extra orbital muscle insertion zone with open eye treatment), or any combination as described elsewhere herein. In some cases, the methods described herein may be conducted by an operator, where the operator may comprise medical personnel, e.g., an optometrist, ophthalmologist, nurse, medical assistant, physician's assistant, family medicine physician, internal medicine physician, or any combination thereof.

In some instances, the method of treating an ocular condition 140 may comprise the steps of: (a) providing an anesthetic to a patient receiving an eye treatment 142; (b) placing the patient into mechanical constraints 144; (c) coupling the device to the patient's eye 146; (d) verifying alignment of the device with respect to the patient's eye 148; (e) initiating the device light source emission to treat the patient's eye 150; and (f) uncoupling the device from the patient's eye 152. In some cases, the anesthetic provided to the patient may comprise a topical anesthetic. In some instances, the topical anesthetic may comprise proparacaine, tetracaine, benoxinate cocaine, lidocaine, or any combination thereof. In some cases, the mechanical constraints that the patient is placed into may comprise a chin rest, chin strap, head band strap, or any combination thereof. In some instances, the device may be used in a handheld, in combination with a slit lamp, or a combination thereof. The mechanical constraints may be utilized to stabilize the patient and prevent unnecessary movement during the treatment. In some instances, the device may couple with the eye of the patient to stabilize the device during treatment. In some cases, the device may couple with the eye of the patient through a docking feature described elsewhere herein. In some cases, the alignment of the device with respect to the patient's eye may be achieved by alignment systems described elsewhere herein (e.g., a quad-photodiode optical alignment system). In some instances, the initiation of the emission of the light source may be accomplished by pressing a laser treatment pedal, button, or any combination thereof in electrical communication with the device. In some cases, the initiation of the emission of the light source may be terminated by the operator when the alignment of the system or power of the light source fluctuates to levels that exceed safety thresholds. In some cases, the initiation of the emission of the light source may be manually terminated by the operator by pressing a laser treatment stop pedal, button, or any combination thereof.

In some cases, the method of treating an ocular condition 140 may need to be repeated for one or more treatments to achieve a therapeutic effect. Alternatively, a single treatment may be sufficient to produce a desirable therapeutic effect. In some cases, the time period between treatments may comprise one or more days, one or more weeks, one or more months, one or more years, or any combination thereof.

Although the above steps show method 140 and 154 in accordance with embodiments, a person of ordinary skill in the art will recognize many variations based on the teaching described herein. The steps may be completed in a different order. Steps may be added or omitted. Some of the steps may comprise sub-steps. Many of the steps may be repeated as often as beneficial.

One or more of the steps of method 140 and/or 154 may be performed with circuitry as described herein, for example, one or more processors or logic circuitry such as programmable array logic for a field programmable gate array. The circuitry may be programmed to perform one or more of the steps of the method 140 and/or 154, and the program may comprise program instructions stored on a computer readable memory or programmed steps of the logic circuitry such as the programmable array logic or the field programmable gate array, for example.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for treating an eye, the system comprising:
a laser configured to generate a laser beam; and
a diffractive optical element configured to split the laser beam into a pre-determined pattern and direct the patterned laser beam to a treatment zone of the eye
wherein the system is a portable laser system and
wherein the diffractive optical element is configured to transform the input laser light in a manner that produces a curved wave front emitted beam.

2. The system of claim 1, wherein the laser comprises a near-IR to mid-IR laser.

3. The system of claim 1, wherein the laser comprises a wavelength range from 500 nanometers (nm) to 2 micrometers (um).

4. The system of claim 1, wherein the laser comprises a power from 100 (milliwatts) mW to 4 watts (W).

5. The system of claim 1, wherein the laser comprises a pulse repetition rate from 1 hertz (Hz) to 1000 Hz.

6. The system of claim 1 wherein the pre-determined pattern comprises an arcuate, annular, spotted, or line scan pattern.

7. The system of claim 6, wherein the spotted pattern comprises at least 2 points of illumination.

8. The system of claim 1, wherein the treatment zone of the eye comprises the eyelids, sclera, retina, or any combination thereof.

9. The system of claim 1, wherein the system is configured to be handheld or slit lamp adapted.

10. A method for treating an eye with a system, the method comprising:
generating a laser beam;
splitting the laser beam into a pre-determined pattern with a diffractive optical element; and
directing the patterned laser beam to a treatment zone of the eye, thereby treating a target tissue in the treatment zone with the patterned laser beam
wherein the system is a portable laser system and
wherein the diffractive optical element is configured to transform the input laser light in a manner that produces a curved wave front emitted beam.

11. The method of claim 10, wherein the laser beam comprises a near-IR to mid-IR laser emission.

12. The method of claim 10, wherein the laser beam comprises a wavelength range from 500 nanometers (nm) to 2 micrometers (t·tm).

13. The method of claim 10, wherein the laser beam comprises a power from 100 (milliwatts) mW to 4 watts (W).

14. The method of claim 10, wherein the laser beam comprises a pulse repetition rate from 1 hertz (Hz) to 1000 Hz.

15. The method of claim 10, wherein the pre-determined pattern comprises an arcuate, annular, spotted, or line scan pattern.

16. The method of claim 10, wherein the treatment may comprise a treatment for dry eye, diplopia, convergence insufficiency, strabismus, or any combination thereof.

17. The method of claim 10, further comprising aligning the patterned laser beam to irradiate the treatment zone of the eye wherein aligning comprises determining one or more optical signals on an alignment sensor.

18. The method of claim 17, wherein the one or more optical signals comprise one or more reflected optical signal from a cornea, iris, or any combination thereof a patient.

19. The method of claim 17, wherein the one or more optical signals comprise near-infrared (NIR) illumination, visible illumination, or any combination thereof.

20. The method of claim 19, wherein the near-infrared illumination comprises a wavelength range from 850 nanometers (nm) to 940 nm.

* * * * *